(12) United States Patent
Bauchot et al.

(10) Patent No.: US 10,852,144 B2
(45) Date of Patent: *Dec. 1, 2020

(54) ANALYSIS OF PEDESTRIAN CONGESTION

(71) Applicant: NEC CORPORATION, Tokyo (JP)

(72) Inventors: Frederic Bauchot, Saint-Jeannet (FR); Jean-Yves Clement, Saint-Jeannet (FR)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/531,999

(22) Filed: Aug. 5, 2019

(65) Prior Publication Data

US 2019/0360814 A1 Nov. 28, 2019

Related U.S. Application Data

(63) Continuation of application No. 15/011,792, filed on Feb. 1, 2016, now Pat. No. 10,436,592, which is a
(Continued)

(51) Int. Cl.
*G01C 21/20* (2006.01)
*G01P 13/00* (2006.01)
(Continued)

(52) U.S. Cl.
CPC .............. *G01C 21/20* (2013.01); *A61B 5/112* (2013.01); *A61B 5/6807* (2013.01); *G01C 21/00* (2013.01);
(Continued)

(58) Field of Classification Search
CPC ........ G01C 21/20; A61B 5/112; A61B 5/6829
See application file for complete search history.

(56) References Cited

U.S. PATENT DOCUMENTS 6,175,608 B1 1/2001 Pyles et al.
6,473,483 B2 10/2002 Pyles
(Continued)

FOREIGN PATENT DOCUMENTS

JP 2000227342 8/2000
JP 2010085285 4/2010
(Continued)

OTHER PUBLICATIONS

Jang, Y. et al, "A Preliminary Study for Portable Walking Distance Measurement System Using Ultrasonic Sensors", Proceedings of the 29th Annual International Conference of the IEEE EMBS, Cite Internationale, Lyon, France, Aug. 23-26, 2007.
(Continued)

*Primary Examiner* — Michael J Dalbo
(74) *Attorney, Agent, or Firm* — Sughrue Mion, PLLC

(57) ABSTRACT

A method, system and computer program product are disclosed for providing a measure of pedestrian congestion in a given area. In one embodiment, the method comprises collecting data from a pedestrian moving in the area, and using the data to determine one or more specified parameters representing a pattern of movement of the pedestrian in the area. These specified parameters are used to determine a sinuosity of pedestrian traffic in the given area. In one embodiment, the pattern of movement is a walking pattern of the pedestrian, and the data collected from the pedestrian identifies a multitude of positions of the pedestrian's feet. In an embodiment, the specified parameters include a lateral gap between the feet of the pedestrian, and a length of a stride of the pedestrian. A sequence of values may be collected for each of these parameters.

20 Claims, 8 Drawing Sheets

Related U.S. Application Data continuation of application No. 13/861,991, filed on Apr. 12, 2013, now Pat. No. 9,285,388.

(51) Int. Cl.
  *G08G 1/01* (2006.01)
  *G01C 22/00* (2006.01)
  *A61B 5/00* (2006.01)
  *A61B 5/11* (2006.01)
  *G01C 21/00* (2006.01)

(52) U.S. Cl.
  CPC .............. *G01C 22/00* (2013.01); *G01P 13/00* (2013.01); *G08G 1/01* (2013.01); *G08G 1/0104* (2013.01)

(56) References Cited

U.S. PATENT DOCUMENTS

| | | | |
|---|---|---|---|
| 7,328,131 | B2 | 2/2008 | Donofrio et al. |
| 7,526,404 | B2 | 4/2009 | Ihashi |
| 7,747,409 | B2 | 6/2010 | Ladetto et al. |
| 7,747,411 | B2 | 6/2010 | Kato |
| 9,285,388 | B2 | 3/2016 | Bauchot et al. |
| 10,436,592 | B2 * | 10/2019 | Bauchot ............... G01C 21/00 |
| 2007/0285306 | A1 * | 12/2007 | Julian ................ G01S 13/765 342/118 |
| 2009/0326795 | A1 | 12/2009 | Supino et al. |
| 2010/0004860 | A1 | 1/2010 | Chernoguz et al. |
| 2010/0045508 | A1 * | 2/2010 | Ekbal ................ G01S 13/765 342/145 |
| 2010/0185411 | A1 | 7/2010 | Pfeiffer et al. |
| 2011/0184225 | A1 * | 7/2011 | Whitall .............. A63B 24/0003 600/28 |
| 2011/0210866 | A1 | 9/2011 | David et al. |
| 2013/0041617 | A1 | 2/2013 | Pease et al. |
| 2013/0123665 | A1 * | 5/2013 | Mariani ............... A61B 5/6807 600/592 |
| 2014/0129189 | A1 | 5/2014 | Gyorfi |
| 2014/0207374 | A1 * | 7/2014 | Taylor, Jr. ........... G01C 21/206 701/470 |
| 2014/0309962 | A1 | 10/2014 | Bauchot et al. |
| 2016/0146613 | A1 | 5/2016 | Bauchot et al. |

FOREIGN PATENT DOCUMENTS

| | | |
|---|---|---|
| WO | WO0068642 | 11/2000 |
| WO | WO2010013745 A1 | 2/2010 |
| WO | WO2012111138 | 8/2012 |

OTHER PUBLICATIONS

Steffen, B., et al., "Methods for measuring pedestrian density, flow, speed and direction with minimal scatter", Physica A 389 (2010) 1902-1910.

Wahab, Y., et al., "Analysis of foot-to-ground clearance measurement techniques for MEMS realization", Computer and information technology, 2007, iccit 2007, 10th international conference on Dec. 27-29, 2007.

Teknomo, K., et al., "Tracking System to Automate Data Collection of Microscopic Pedestrian Traffic Flow", Proceeding of The 4th Eastern Asia Society for Transportation Studies, Oct. 2001, Hanoi, Vietnam, vol. 3 No. 1, pp. 11-25.

Seyfried, A., et al. "The Fundamental Diagram of Pedestrian Movement Revisited", Journal of Statistical Mechanics: Theory and Experiment, Oct. 2005, vol. 2005.

Lu Y.-J., et al., "Measurement of Pedestrian Flow Data Using Image Analysis Techniques", Transportation Research Record, Publication Date: 1990, No. 1281, p. 87-96.

Daamen, W., et al., "Flow-Density Relations for Pedestrian Traffic", Traffic and Granular Flow'May 2007, Part III, 315-322.

Dean et al., "The Effect of Lateral Stabilization on Walking in Young and Old Adults", IEEE Transactions on Biomedical Engineering, vol. 54, No. 11, Nov. 2007, pp. 1919-1926.

\* cited by examiner

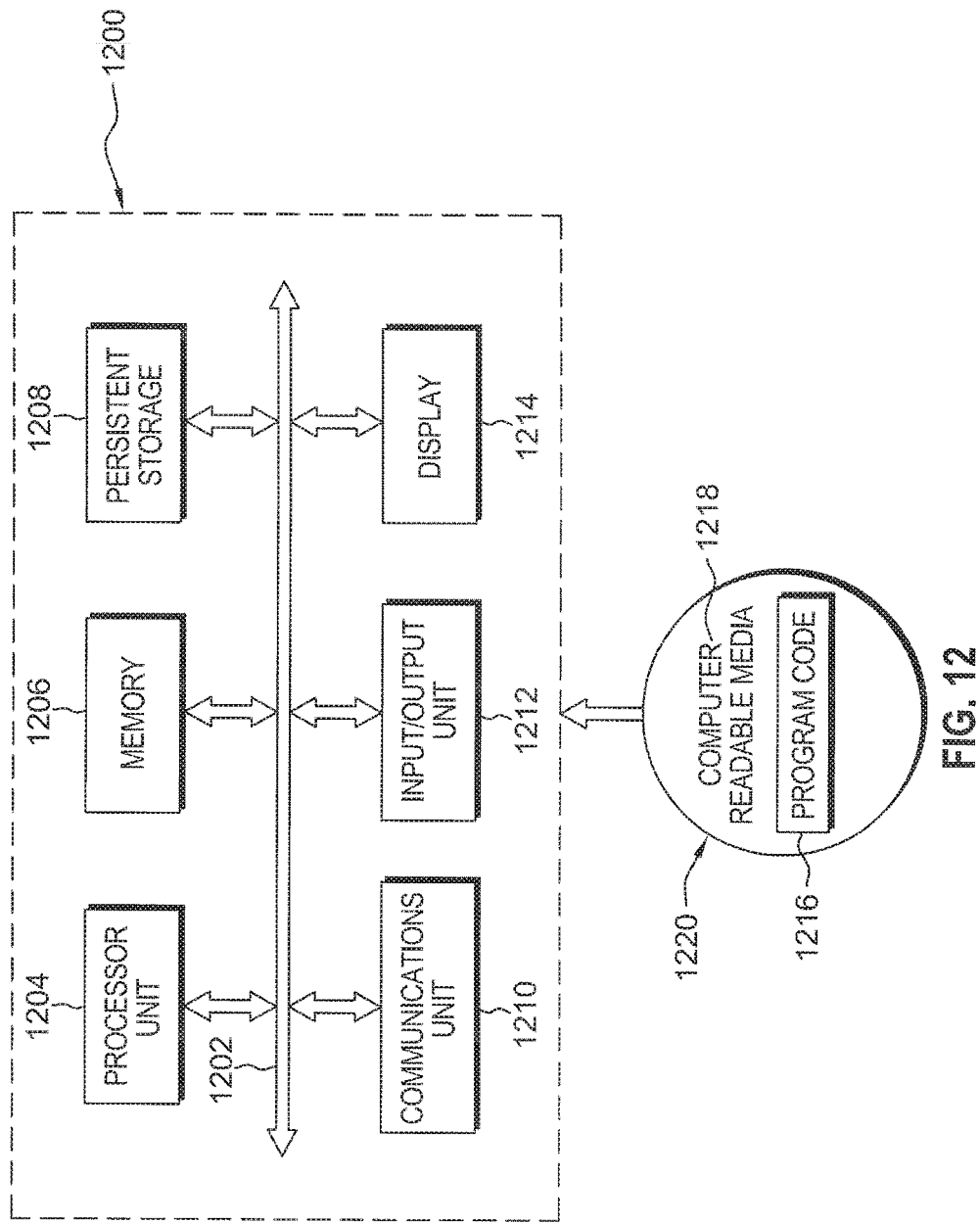

ANALYSIS OF PEDESTRIAN CONGESTION

CROSS REFERENCE TO RELATED APPLICATIONS

This application is a continuation of U.S. patent application Ser. No. 15/011,792, filed Feb. 1, 2016, which is a continuation of U.S. patent application Ser. No. 13/861,991, filed Apr. 12, 2013. The entire content and disclosure of U.S. patent application Ser. Nos. 15/011,792 and 13/861,991 are hereby incorporated herein by reference.

BACKGROUND

This invention generally relates analyzing pedestrian congestion, and more specifically to providing one or more measures of pedestrian congestion.

More and more, smart transportation systems integrate the "transport multi-modality" where a commuter can use multiple transportation means such as cars, bicycles, busses, trains and walking. Walking is very important because people can almost never assume that all the other transportation means will bring a person to the final destination without having to do at least some walking. Understanding the walking conditions, or the "fluidity" of walking, is important so that personal transportation journey advisors can guide people precisely and efficiently.

The time needed for a given pedestrian P to walk from point A to point B depends on three factors: the distance between the two points A and B; the walking characteristics of the pedestrian P; and the fluidity of the pedestrian traffic. The walking characteristics of the pedestrian mainly relate to his or her regular walking speed v. The fluidity of the pedestrian traffic is a measure of the amount of obstacles (such as other pedestrians) that prevent a person from freely walking or marching.

BRIEF SUMMARY

Embodiments of the invention provide a method, system and computer program product for providing a measure of pedestrian congestion in a given area. In one embodiment, the method comprises collecting data from a pedestrian moving in said given area, and using said data to determine one or more specified parameters representing a pattern of movement of the pedestrian in the given area. The one or more specified parameters are used to determine a sinuosity of pedestrian traffic in the given area.

In one embodiment, the pattern of movement is a walking pattern of the pedestrian, and the data collected from the pedestrian identifies a multitude of positions of the feet of the pedestrian.

In an embodiment, the one or more specified parameters include one parameter, e, representing a lateral gap between the feet of the pedestrian; and another parameter, l, representing a length of a stride of the pedestrian.

In one embodiment, a first series of values $\{e_i\}$ is collected for e, and a standard deviation of these first series of values is determined.

In an embodiment, a second series of values $\{l_i\}$ is collected for l.

In one embodiment, this second series of values is used to calculate an average stride length for the pedestrian.

In an embodiment, one or more samples of the second series of values are used to calculate this average stride length; and the standard deviation of the first series of values is used to determine said one or more samples of the second series of values.

In one embodiment, a stride and gap series $\{\sqrt{l_i+e_i}\}$ is computed and used to determine a defined variable representing movement of the pedestrian in the given area.

In one embodiment, the sinuosity of pedestrian traffic is determined by using the standard deviation of the first series of values.

In an embodiment, the sinuosity, s, is determined as a function of said standard deviation σ(s) using the equation:

$$\sigma(s) = \frac{1}{ds^2}\left[1\ \sqrt{s^2-1^{\square}}\ + e(1-s)\right]$$

where d is a distance between defined obstacles in the walking path of the pedestrian.

BRIEF DESCRIPTION OF THE SEVERAL VIEWS OF THE DRAWINGS

FIG. 12 illustrates a computer system that may be used as a server or client in the environment shown in FIG. 11.

DETAILED DESCRIPTION

Figure 1:
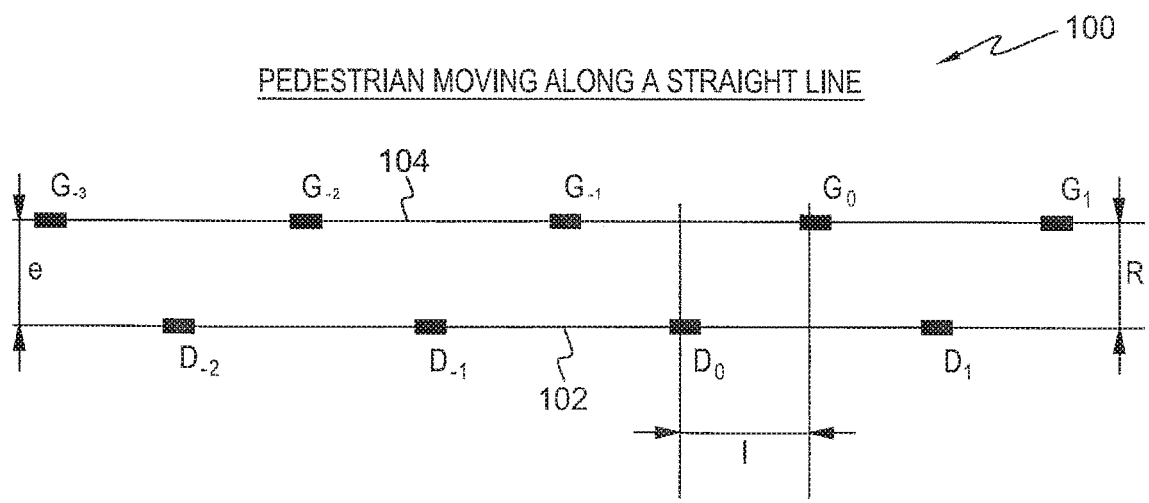
FIG. 1 is a diagram of a path taken by a pedestrian moving along a straight line.

As will be appreciated by one skilled in the art, embodiments of the present invention may be embodied as a system, method or computer program product. Accordingly, embodiments of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, embodiments of the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The present invention relates to analyze pedestrian congestion in a given area. The analysis can be used to advise people on the pedestrian traffic in that area and to help guide people who are walking through the area.

As mentioned above, the time needed for a given pedestrian P to walk from point A to point B depends on three factors: the distance between the two points A and B; the walking characteristics of the pedestrian P; and the fluidity of the pedestrian traffic. The walking characteristics of the pedestrian mainly relate to his or her regular walking speed v. The fluidity of the pedestrian traffic is a measure of the amount of obstacles (such as other pedestrians) that prevent a person from freely walking or marching.

The latter parameter is referred to as the "sinuosity," noted as "s," of the ground, and is measured as the ratio of the distance a person actually walks between points A and B to the geometric, or straight line, distance between those two points. Without any obstacles in the pedestrian's path, s=1. With obstacles in the path, s>1.

The time, t, needed by the pedestrian to walk from the point A to the point B, is determined as:

$$t = \frac{d(A, B)}{v} \times s$$

d(A,B) is known from A and B;
s is determined, as discussed in detail below; and
v is associated with the pedestrian.

Embodiments of the invention provide a model driven by the successive positions of the right and left feet of the pedestrian.

FIG. 1 shows a path 100 of a pedestrian moving along a straight line. Line 102 represents the path of the pedestrian's right foot, and line 104 represents the path of the pedestrian's left foot. In this FIG., $D_i$ represents successive positions of the right foot on the ground;

$G_i$ represents successive positions of the left foot on the ground;

e and l are parameters characterizing the walking pattern of the pedestrian; e is the lateral distance, referred to as the "gap," between the line of the right foot and the line of the left foot at various points along the path 100; l is the longitudinal distance, referred to as the "stride," between successive positions of the right and left feet—that is, between a position of one of the feet and the next position of the other foot, for example between positions $G_{-2}$ and $D_{-1}$.

If there are no obstacles in the way, the pedestrian walks in a relatively constant, straight way, so the parameters e and l remain almost constant. This means that, typically, the standard deviations of the series of gap values $\{e_i\}$ and the series of stride values $\{l_i\}$ remain quite low, although not zero.

Figure 2:
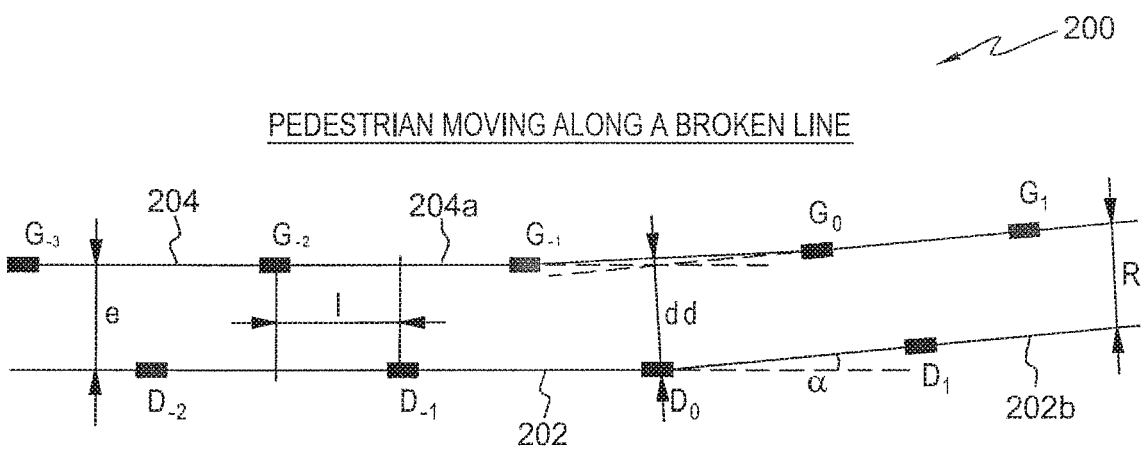
FIG. 2 is a diagram of a pedestrian path that is not a straight line.

FIG. 2 shows a path 200 taken by a pedestrian when he or she does not walk in a straight line. This path walked by the pedestrian may be referred to as a broken line. In FIG. 2, line 202 represents the line of the pedestrian's right foot, and line 204 represents the line of the pedestrian's left foot.

In the example of FIG. 2, e, as measured just forward of $G_{-3}$ and just forward of $G_1$, is constant, and l is also constant. The gap between the lines of the left and right feet increases slightly at point $D_0$. The length of this gap, dd, can be determined from trigonometry as a function of the angle, $\alpha$, between line segments 204a and 202b.

$$dd = 1\ \sin\frac{(\alpha)}{2} + e\ \cos\frac{(\alpha)}{2}$$

If $\alpha = o$, then dd=e: which means lines 202 and 204 are straight, as in FIG. 1;

If $\alpha > 0$, and $\alpha$ remains small, $$dd \cong e + 1\frac{(\alpha)}{2};$$

and dd is slightly greater than e;

If $\alpha < 0$ and $\alpha$ remains small, $$dd \cong e - 1\frac{(\alpha)}{2};$$

and dd is slightly less than e.

Figure 3:
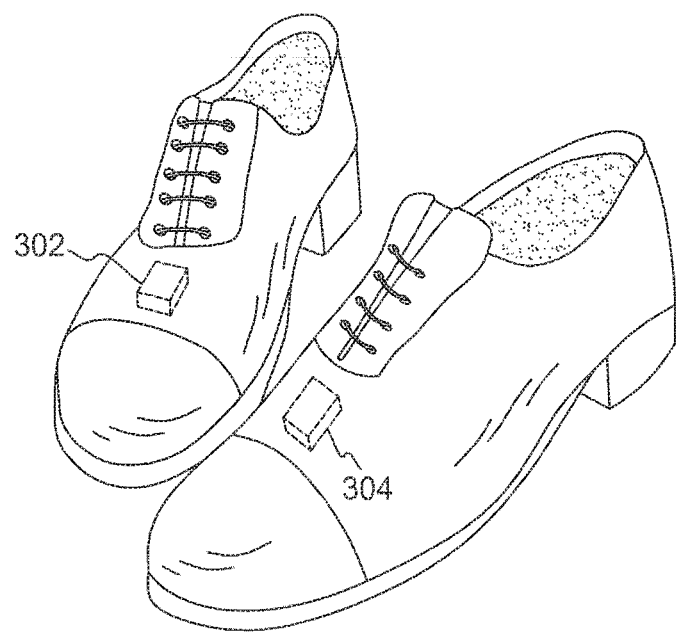
FIG. 3 shows transducers mounted on the feet of a person in order to measure distance between those feet.

Aspects of a walking model are discussed below with reference to FIGS. 3-5.

Embodiments of the invention use shoe mounted transceivers to measure movement of a person's feet. With reference to FIG. 3, in one embodiment, each shoe is equipped with a transceiver: one of these transceivers is a primary transceiver 302, and the other is a secondary transceiver 304. To measure foot movement and related distances, the primary transceiver transmits a train of pulses at frequency F1, with a rate R1, starting a timer count at each pulse. As a typical example, R1=10 Hz.

The secondary transceiver, upon reception of a pulse from the primary transceiver at frequency F1, waits for a fixed, very short delay t (for example, 0.1 us) and then transmits a pulse at a frequency F2. Upon reception of a pulse F2, the primary transceiver records the timer count T and then waits for the next R1 pulse to restart the timer count.

There is a relationship between T and the distance d between the feet: $T = \Delta t + d/s$ In this embodiment, the primary transceiver records the distance d in a table.

Figure 4:
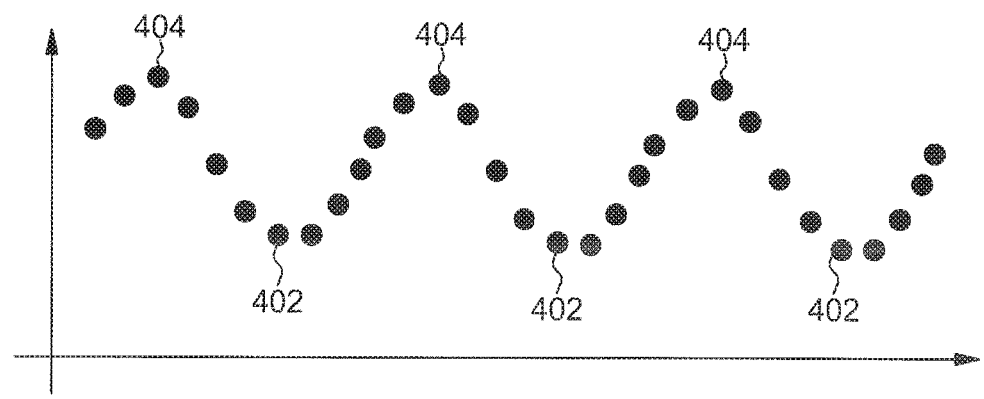
FIG. 4 is a graph showing the distance between the feet of a person as the person is walking.

FIG. 4 is a chart showing one example of the changing distances between the feet of a person as that person walks. The maximum distance between the feet usually occurs when one foot that had been moving comes to rest on the ground, ahead of the other foot. The minimum distance between the feet usually occurs when the moving foot is immediately to the side of the stationary foot.

The "gap" serie $\{e_i\}$ corresponds to the minimas of the foot distances 402. The "gap & stride" series corresponds to the maximas of the foot distances 404.

The primary transceiver 302 determines the successive maximas and minimas from the recorded foot distance samples (possibly with interpolation). For each triplet of successive Min-Max-Min distance values, the primary receiver computes the corresponding walking distance, and related distances, using trigonometry.

Figure 5:
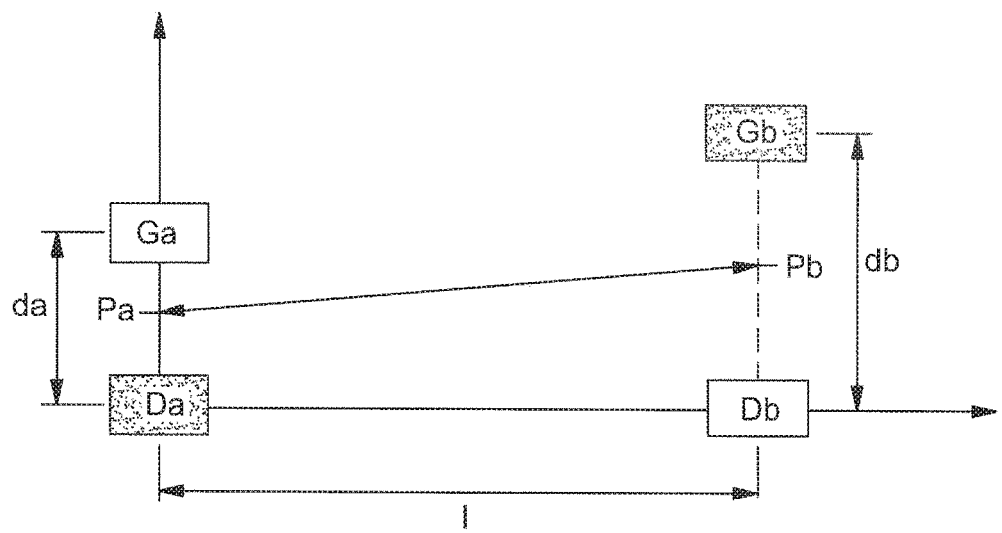
FIG. 5 show various feet positions and distances as a person walks along a path.

FIG. 5 shows four of the feet positions of a walking person. At time t0, the right foot of the person is stationary on the ground at Da, and the left foot is at Ga and is moving past the right foot. At time t1, both feet are stationary on the ground, with the right foot at Da and the left foot at Gb. At this point, the person begins to move the right foot; and at time t2, the right foot is at Db, directly to the side of the left foot.

As represented in FIG. 5, the length of the person's stride is 1, and the distance walked from t0 to t2 is distance (Pa Pb). The person's foot gap at t0 is da, and the foot gap at t2 is db, and, as can be seen, this foot gap increases from t0 to t2.

At t0, the distance between the feet is:

$$DaGa, d(t0) = \sqrt{da^2 + k^2},$$

where k is the elevation of the left foot above the ground.

At time t1, the distance between the feet is:

$$DaGb, d(t1) = \sqrt{l^2 + db^2}$$

At time t2, the distance between the feet is:

$$DbGb, d(t2) = \sqrt{db^2 + k^2}$$

The distance, w, walked by the person from t0 to t2 is:

$$W = d(Pa, Pb) = \sqrt{\frac{d_1^2 - d_2^2 + k^2 + \left(\sqrt{d_0^2 - k^2} - \sqrt{d_2^2 - k^2}\right)^2}{4}}$$

Figure 6:
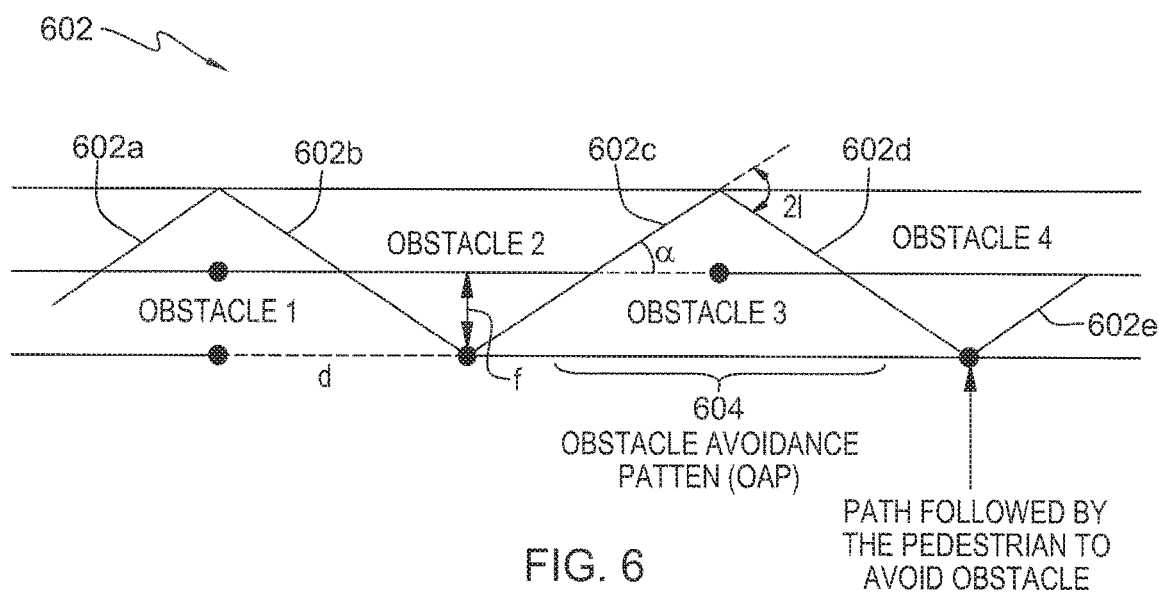
FIG. 6 shows a path taken by a pedestrian to avoid several obstacles.

FIG. 6 shows a path 602 of a pedestrian as he or she walks past several obstacles in a given area. A number of parameters are shown in this FIG., including d, f, l and $\psi$. d is the distance between successive obstacles. f is the free space between the pedestrian and an obstacle as the pedestrian passes the obstacle. A typical value is 0.5 m. l is the length of the stride of the pedestrian. A typical value is 0.75 m. $\psi$ is the angle between a straight line path that the pedestrian would take if there were no obstacles and the individual path segments 602a, 602b, 602c, 602d, 602e along which the pedestrian actually walks to avoid the obstacles.

F, d and $\psi$ are related as follows:

$\tan \psi = 2f/d$ and $s = 1/\cos \psi$.

Also, along the portion of the path designated at 604 and referred to as the Obstacle Avoidance Pattern (OAP), the total number of strides, N, taken by the pedestrian is given by the equation:

$N = d/l \cos \psi$.

These N strides are comprised of N−1 straight strides with foot gap $e_i = e$, and 1 curved stride with foot gap $e_i = e \cos \psi + l \sin \psi$.

$$E(e_i) = \frac{l \cos \Psi}{d}\ [l \sin \Psi + e\ (\cos \Psi - 1)] + e$$

Figure 7:
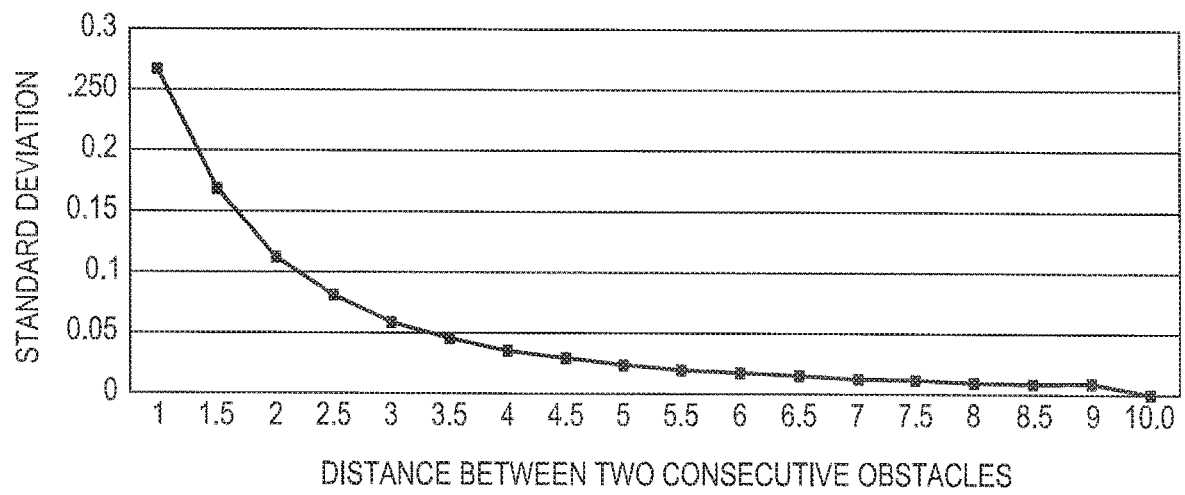
FIG. 7 is a chart showing the standard deviation of a gap in a pedestrian's stride as a function of the distance between two consecutive obstacles.
Figure 8:
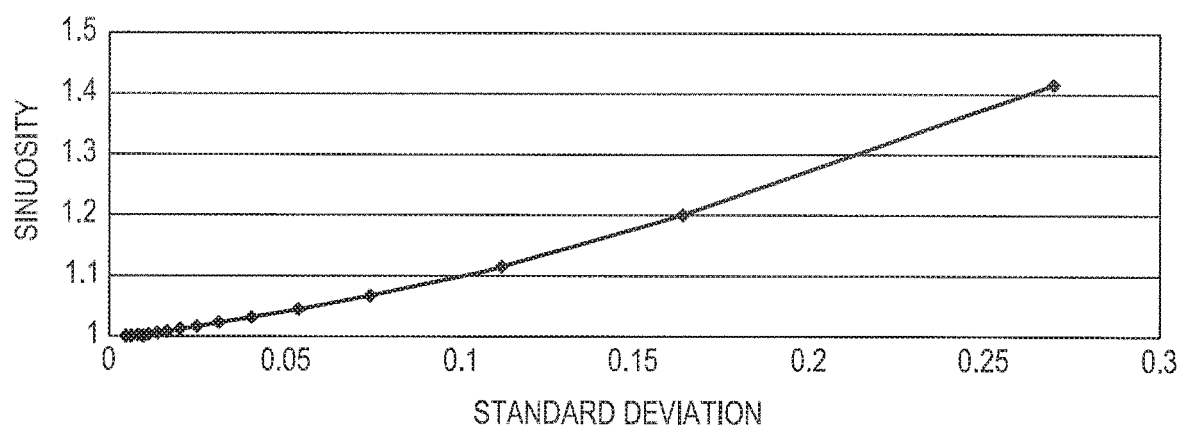
FIG. 8 is a chart showing the sinuosity of pedestrian traffic as a function of the standard deviation shown in the chart of FIG. 7.

With reference to FIGS. 7 and 8, the standard deviation of the gap e, expressed in terms of the distance between two consecutive obstacles, is:

$$\sigma = \frac{l}{sd}[l \sin \Psi + e (\cos \Psi - 1)]$$

Or, expressed as a function of sinuosity, s, $$\sigma(s) = \frac{1}{ds^2}[1 \sqrt{s^2 - 1} + e(1-s)]$$

The above-discussion modelizes the effect of pedestrian traffic congestion by a trajectory made of a succession of broken lines for avoiding collisions with other pedestrians. This leads to a series of gap measurements $\{e_i\}$ with an increasing standard deviation. The formula above gives the relation between the standard deviation and the increase in the distance to walk between two obstacles.

When the pedestrian traffic becomes more and more congested, a second effect (after the one modelized above) is a decrease of the pedestrian's stride length. As the number of strides per unit of time, referred to as the marching frequency, is approximately constant for a given person, the decrease in the stride length has a linear effect on the time taken to walk a given distance. Accordingly, embodiments of the invention monitor the average value of a parameter referred to as the "gap & stride" (the maxima values of the distance between feet) corresponding to $\sqrt{e_i + l_i}$.

In embodiments of the invention, the transceivers are used to measure over time the distance between the feet of the pedestrian and to record the serie of minima (the "gap" serie $\{e_i\}$) and the serie of maxima (the "stride & gap" serie $\{\sqrt{l_i + e_i}\}$).

An average value "L" of the stride serie $\{l_i\}$, for the samples where the standard deviation of the gap serie $\{e_i\}$ remains below a threshold "Σ", is determined and stored in memory. This average stride value "L" corresponds to the pedestrian's stride in normal traffic condition, without congestion.

Embodiments of the invention compute, over a specified subset of the recorded series, the standard deviation σ of the gap serie $\{e_i\}$, the average value of the stride serie $\{l_i\}$ the parameter L. These values L and σ may be stored in memory. In embodiments of the invention, the above-identified values may be computed in response to a request, and the computed values may be returned to the requestor.

Figure 9:
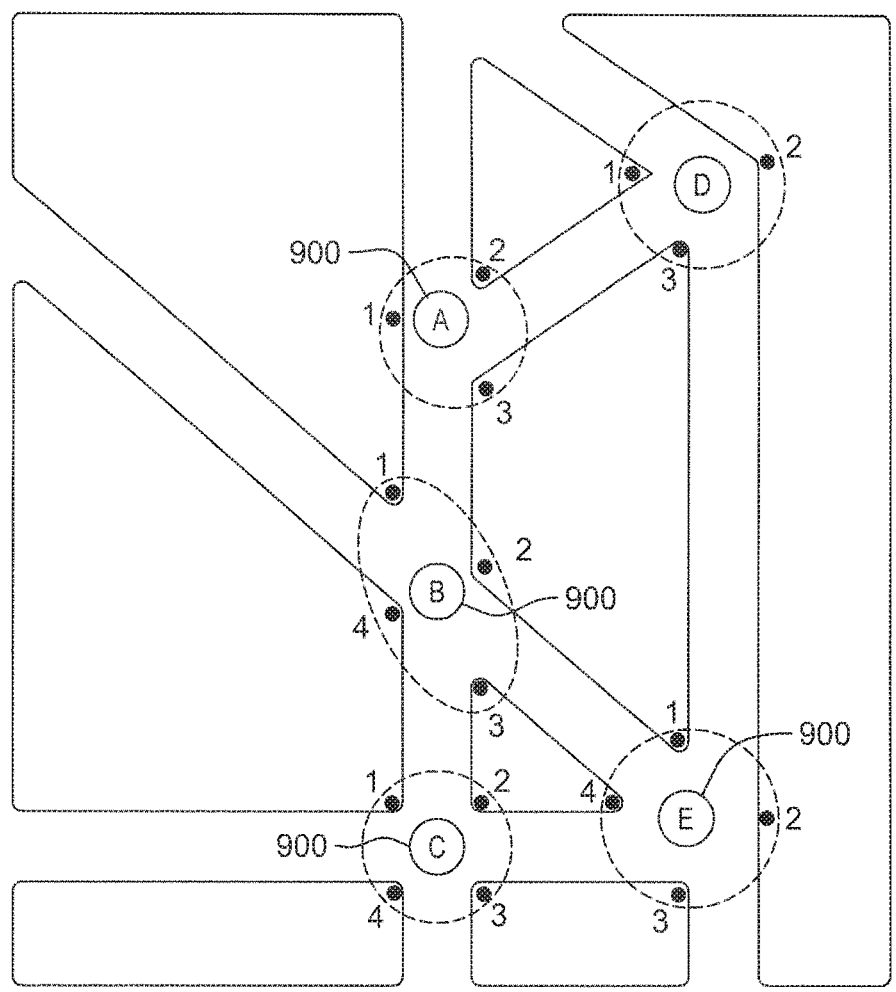
FIG. 9 depicts a group of meters used to monitor pedestrian congestion.

With reference to FIG. 9, embodiments of the invention provide one or more pedestrian traffic jam meters 900 that, for example, may be anchored within a smart city transportation infrastructure. Each meter is, in embodiments of the invention, configured to request and receive information from pedestrian foot transceivers, as described above, and to compute, from a gap serie standard deviation σ, the traffic sinuosity s according to the formula discussed above. The pedestrian traffic meter also computes, from the average stride value divided by the reference stride L, another parameter called compression, c, using the equation:

$$C = \frac{\overline{\{l_i\}}}{L} \quad (c \leq 1)$$

In embodiments of the invention, the pedestrian traffic meter also computes an overall pedestrian traffic congestion slow down factor, S=s/c (≥1). S may be used as a time scaling factor $T_{congestion}$, for evaluating the time needed by a Pedestrian to move from point A to point B.

$$T_{congestion} = T_{normal} \times S$$

Each meter 900 is uniquely identified by a meter ID and an index (e.g. A.1), and meters belonging to the same measurement point share the same meter ID. The meters are equipped with communication means, typically wireless ones, for broadcasting the meters signature (ID, index) through a beacon. The foot transceivers on the pedestrians continuously monitor for the presence of meters by listening for the beacons issued by the meters. The foot transceivers also are continuously monitoring the pedestrian's stride information, as explained above, by recording a series of stride information samples.

Figure 10:
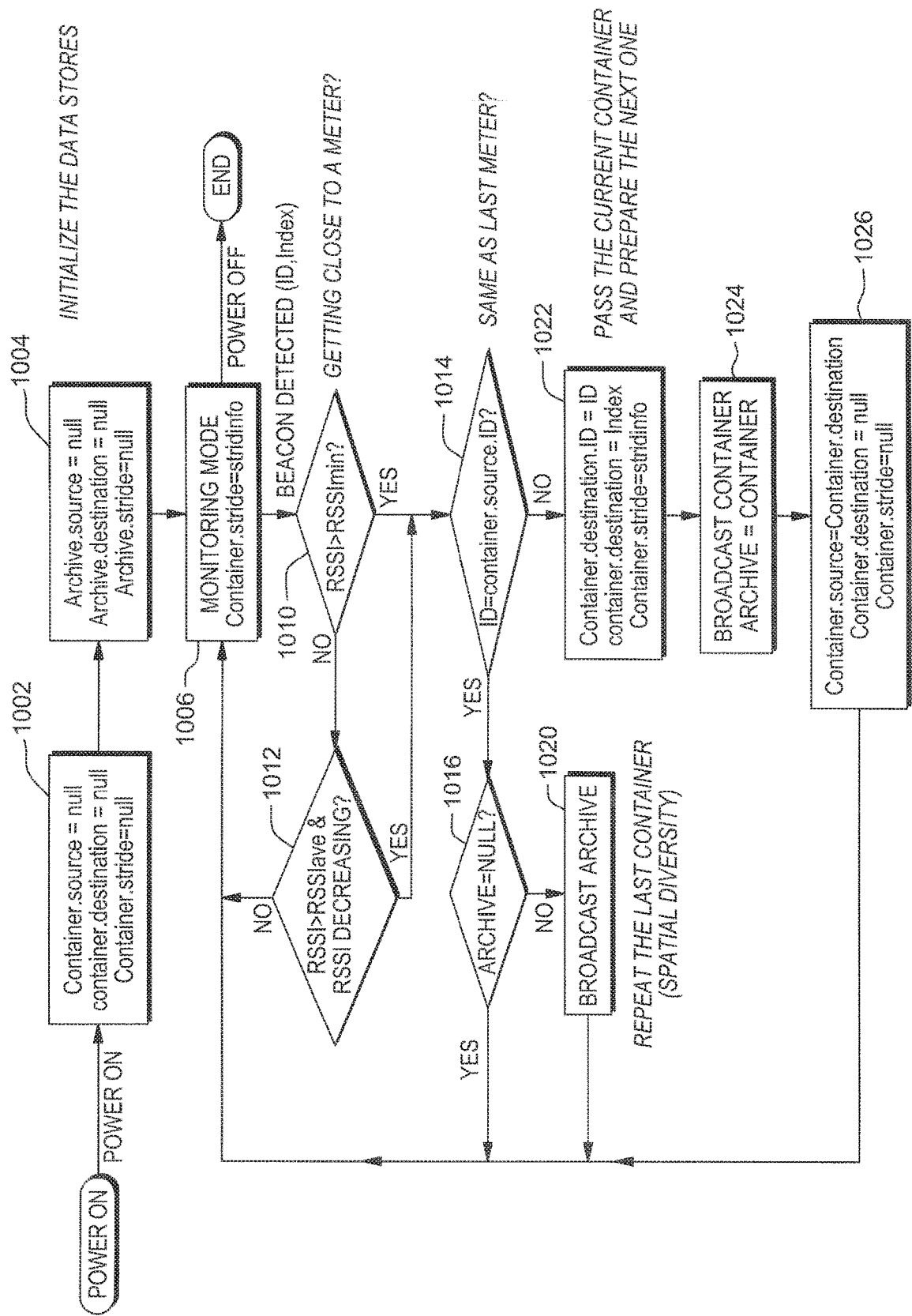
FIG. 10 is a flow chart illustrating an operation of an embodiment of the invention.

FIG. 10 is a flow chart showing, as an example, one embodiment of the invention, and, more specifically, the way in which an embodiment of the invention may be implemented in the environment shown in FIG. 9. As illustrated in FIG. 10, after the foot transceivers are powered on, data stores in the transceivers are initialized at 1002 and 1004. At step 1002, three sets of fields, referred to as container.source, container.destination, and container.stride, are set to null values. The container.source fields are used to store current data from the transceivers 302, 304. The container.destination fields are used to store data that is ready to be sent to one of the jam meters, and container.stride fields are used to store current stride values. At step 104, three sets of fields, referred to as archive.source, archive.destination and archive.stride, are set to null values. The archive.source fields are used to archive data collected from the transceivers. Archive.destination fields are used to archive data sent to one of the jam meters, and archive.stride fields are used to archive stride values.

At 1006, the transceivers 302, 304 monitor for a beacon from one of the jam meters 900 and also current stride information is stored at container stride. If no beacon is detected, the transceiver powers-off.

If a beacon is detected, then, at 1010, the strength of the beacon the received signal strength indicator (RSSI) is compared to a minimum level (RSSI min). If the beacon strength (RSSI) is not greater than that minimum level, the process moves to step 1012, where the beacon strength is compared to a previously stored value average (RSSI ave) to determine if the beacon strength is decreasing. If the beacon strength is not decreasing, the process returns to the monitoring mode at step 1110. If the beacon strength is decreasing, the process moves on to step 1014. The routine of FIG. 10 also moves on to step 1014 if, at step 1110, the beacon strength is above the set minimum level.

At step 1014, the meter ID is used to determine if that ID is the same as the last detected meter ID. If these two IDs are the same, then at step 1016 the transceiver checks its archive fields to determine if those archive are set to null values. If the archive is not null, the contents of the archive are broadcast to the jam meter, at step 1020, and the routine returns to step 1110. If the archive is null at step 1016, the routine returns directly to the monitoring mode, at step 1110.

If at step 1014, the detected meter is not the same as the previous detected meter, then, at step 1022, a destination ID and index are stored and the current stride information is stored in the container stride fields. At step 1024, the container fields are broadcast to the detected meter and the archive fields are set equal to the container fields. At 1026, the container.source field is set equal to the container.destination field, the container.destination and container.stride fields are set equal to null values, and the routine proceeds to the monitoring mode at step 1006.

Figure 11:
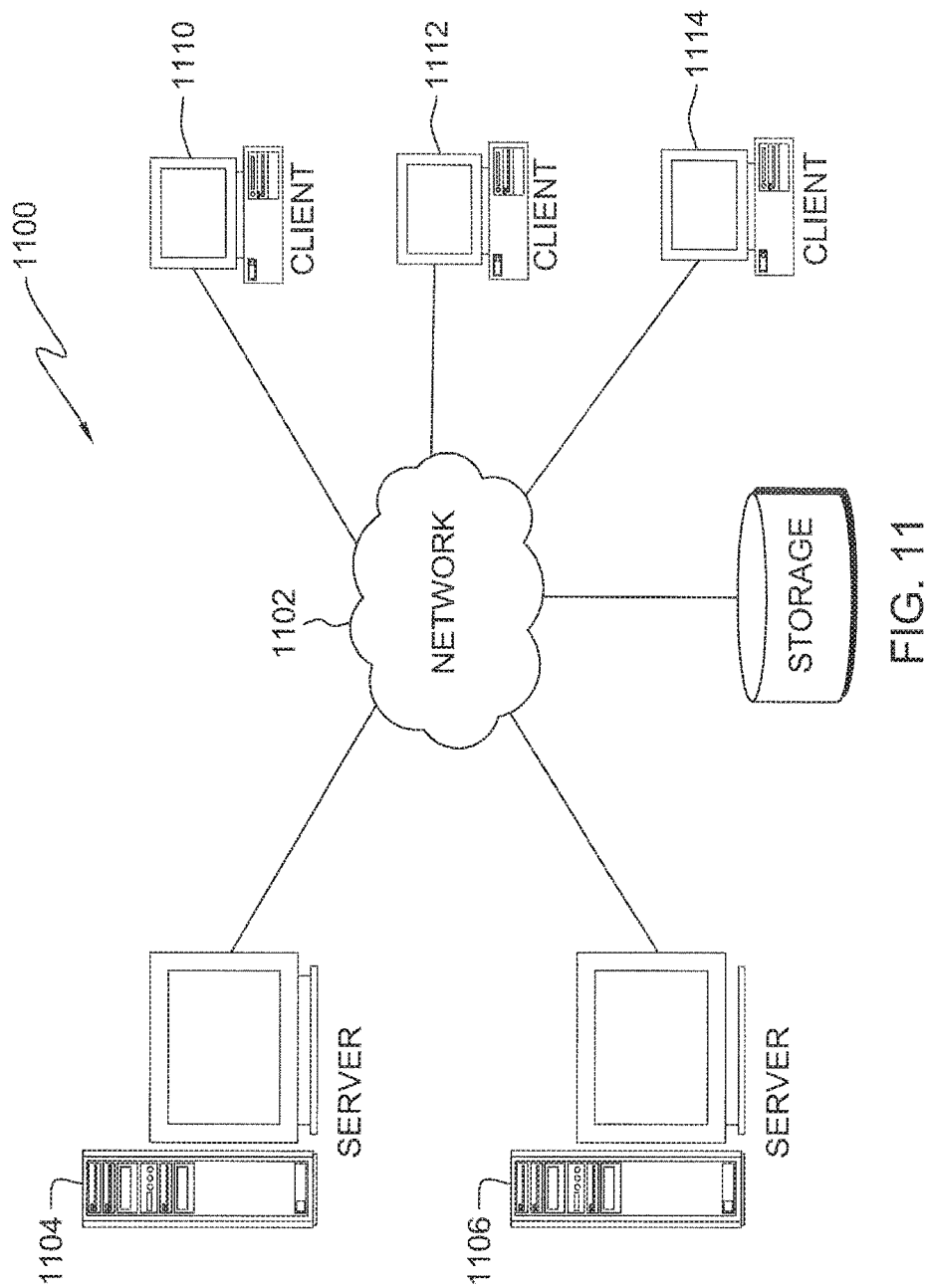
FIG. 11 shows a computing environment in which embodiments of the invention may be implemented.

FIG. 11 depicts a pictorial representation of an exemplary distributed computer system 1100 in which aspects of the illustrative embodiments may be implemented. Distributed system 1100 may include a network of computers in which aspects of the illustrative embodiments may be implemented. The distributed data processing system 1100 contains at least one network 1102, which is the medium used to provide communication links between various devices and computers connected together within 1100. The network 1102 may include connections, such as wire, wireless communication links, or fiber optic cables.

In the depicted example, server 1104 and server 1106 are connected to network 1102 along with storage unit 1108. In addition, clients 1110, 1112, and 1114 are also connected to network 1102. These clients may be, for example, personal computers, network computers, or the like. In the depicted example, server 1104 provides data, such as boot files, operating system images, and applications to the clients 1110, 1112, and 1114. Distributed system 1100 may include additional servers, clients, and other devices not shown.

In the depicted example, the Internet, a worldwide collection of networks and gateways that use the Transmission Control Protocol/Internet Protocol (TCP/IP) suite of protocols to communicate with one another. The distributed system 1100 may also be implemented to include a number of different types of networks, such as for example, an intranet, a local area network (LAN), a wide area network (WAN), or the like. FIG. 11 is intended as an example, not as an architectural limitation, and the particular elements shown in FIG. 11 should not be considered limiting with regard to the environments in which the illustrative embodiments of the present invention may be implemented.

With reference now to FIG. 12, a block diagram of a computer or computer system 1200 is shown. System 1200 is an example of a computer, such as server 1104 or client 1110 in FIG. 11. In this illustrative example, system 1200 includes communications fabric 1202, which provides communications between processor unit 1204, memory 1206, persistent storage 1208, communications unit 1210, input/output (I/O) unit 1212, and display 1214.

Processor unit 1204 serves to execute instructions for software that may be loaded into memory 1206. Processor unit 1204 may be a set of one or more processors or may be a multi-processor core, depending on the particular implementation. Memory 1206 and persistent storage 1208 are examples of storage devices. Memory 1206, in these examples, may be a random access memory or any other suitable volatile or non-volatile storage device. Persistent storage 1208 may take various forms depending on the particular implementation. For example, persistent storage 1208 may be a hard drive, a flash memory, a rewritable optical disk, a rewritable magnetic tape, or some combination of the above.

Communications unit 1210, in these examples, provides for communications with other data processing systems or devices. In these examples, communications unit 1210 is a network interface card. Communications unit 1210 may provide communications through the use of either or both physical and wireless communications links. Input/output unit 1212 allows for input and output of data with other devices that may be connected to data processing system 1200. For example, input/output unit 1212 may provide a connection for user input through a keyboard and mouse. Further, input/output unit 1212 may send output to a printer. Display 1214 provides a mechanism to display information to a user.

Those of ordinary skill in the art will appreciate that the hardware in FIGS. 11 and 12 may vary depending on the implementation. Other internal hardware or peripheral devices, such as flash memory, equivalent non-volatile memory, or optical disk drives and the like, may be used in addition to or in place of the hardware depicted in FIGS. 11 and 12.

What is claimed is:

1. A computer-implemented method of determining an increase in a walking pattern of a pedestrian to avoid obstacles on a path along which the pedestrian is walking, the method comprising:

a plurality of transceivers on the pedestrian generating data relating to the walking pattern of the pedestrian on the path; and using said transceivers, over time, to measure distances between feet of the pedestrian; and wherein the plurality of transceivers include a primary transceiver on a first foot of the pedestrian, and a secondary transceiver on a second foot of the pedestrian; and the using said transceivers, over time, to measure distances between feet of the pedestrian includes the primary transceiver transmitting a train of pulses P1 at a frequency F1, and starting a timer count T at each of selected ones of the pulses, the secondary transceiver, upon receipt of one of the pulses P1 from the primary transceiver, transmitting, after a fixed time delay t, a series of pulse P2 at a frequency F2, at each of a multitude of times, the primary transceiver, upon reception of one of the pulses P2, recording a timer count T, and re-starting the timer count T at the next one of the pulses P1, using the timer counts T and the time delay $\Delta t$ to determine a multitude of the distances d between the feet of the pedestrian, and using said determined distances d to determine an increase in a distance the pedestrian walks on the path to avoid the obstacles.

2. The method according to claim 1, wherein the using the timer counts T and the time delay $\Delta t$ to determine a multitude of the distances d between the feet of the pedestrian includes:

determining a sinuosity s of the walking pattern of the pedestrian; and using said sinuosity s to determine the distances d.

3. The method according to claim 2, wherein the using the timer counts T and the time delay $\Delta t$ to determine the distances d further includes determining the distances d using the equation: $T=\Delta t+d/s$.

4. The method according to claim 1, wherein the using the timer counts T and the time delay $\Delta t$ to determine a multitude of the distances d between the feet of the pedestrian includes recording the distances d in a table.

5. The method according to claim 4, wherein the recording the distances d in a table includes the primary transceiver recording the distances d in the table.

6. The method according to claim 1, wherein the time delay $\Delta t$ is 0.1 µs.

7. The method according to claim 1, wherein the using said determined distances d to determine an increase in a distance the pedestrian walks on the path to avoid the obstacles includes using the determined distances d to compute an average length L for a stride of the pedestrian.

8. The method according to claim 7, wherein the using said determined distances d to determine an increase in a distance the pedestrian walks on the path to avoid the obstacles further includes using the determined distances d to compute a series $(l_i)$ of lengths of the stride of the pedestrian.

9. The method according to claim 8, wherein the using said determined distances d to determine an increase in a distance the pedestrian walks on the path to avoid the obstacles further includes computing a standard deviation for said pedestrian walking pattern, and using said standard deviation to compute the average length L for the stride of the pedestrian.

10. The method according to claim 9, wherein:
using said determined distances d to determine an increase in a distance the pedestrian walks on the path to avoid the obstacles includes using the determined distances d to compute a series of lateral gaps between the feet of the pedestrian; and
the computing a standard deviation includes using said computed series of lateral gaps to compute said standard deviation.

11. A computer system for determining an increase in a walking pattern of a pedestrian to avoid obstacles on a path along which the pedestrian is walking, the computer system comprising:
a plurality of transceivers on the pedestrian to generate data relating to the walking pattern of the pedestrian on the path, the plurality of transceivers including a primary transceiver on a first foot of the pedestrian, and a secondary transceiver on a second foot of the pedestrian; and
said plurality of transceivers being configured for measuring, over time, distances between feet of the pedestrian; and including,
the primary transceiver transmitting a train of pulses PI at a frequency FI, and starting a timer count T at each of selected ones of the pulses,
the secondary transceiver, upon receipt of one of the pulses PI from the primary transceiver, transmitting, after a fixed time delay t, a series of pulse P2 at a frequency F2,
at each of a multitude of times, the primary transceiver, upon reception of one of the pulses P2, recording a timer count T, and re-starting the timer count T at the next one of the pulses P1,
using the timer counts T and the time delay Δt to determine a multitude of the distances d between the feet of the pedestrian, and
using said determined distances d to determine an increase in a distance the pedestrian walks on the path to avoid the obstacles.

12. The computer system according to claim 11, wherein the using the timer counts T and the time delay Δt to determine a multitude of the distances d between the feet of the pedestrian includes:
determining a sinuosity s of the walking pattern of the pedestrian; and
using said sinuosity s to determine the distances d.

13. The computer system according to claim 12, wherein the using the timer counts T and the time delay Δt to determine the distances d further includes determining the distances d using the equation: $T=\Delta t+d/s$.

14. The computer system according to claim 11, wherein the time delay Δt is 0.1 μs.

15. The computer system according to claim 11, wherein the using said determined distances d to
determine an increase in a distance the pedestrian walks on the path to avoid the obstacles includes using
the determined distances d to compute an average length L for a stride of the pedestrian.

16. A computer readable program product comprising: a computer readable medium having a computer program code tangibly embodied therein for determining an increase in a walking pattern of a pedestrian to avoid obstacles on a path along which the pedestrian is walking, the computer program code, when executed in a computer system, performing the following:
receiving, at the computer system, data from a plurality of transceivers on the pedestrian data relating to the walking pattern of the pedestrian on the path; and
using said transceivers, over time, to measure distances between feet of the pedestrian; and wherein
the plurality of transceivers include a primary transceiver on a first foot of the pedestrian, and a secondary transceiver on a second foot of the pedestrian; and
the using said transceivers, over time, to measure distances between feet of the pedestrian includes
the primary transceiver transmitting a train of pulses PI at a frequency FI, and starting a timer count Tat each of selected ones of the pulses,
the secondary transceiver, upon receipt of one of the pulses PI from the primary transceiver, transmitting, after a fixed time delay t, a series of pulse P2 at a frequency F2,
at each of a multitude of times, the primary transceiver, upon reception of one of the pulses P2, recording a timer count T, and re-starting the timer count T at the next one of the pulses P1,
using the timer counts T and the time delay Δt to determine a multitude of the distances d between the feet of the pedestrian, and using said determined distances d to determine an increase in a distance the pedestrian walks on the path to avoid the obstacles.

17. The computer readable program product according to claim 16, wherein the using the timer counts T and the time delay Δt to determine a multitude of the distances d between the feet of the pedestrian includes:
determining a sinuosity s of the walking pattern of the pedestrian; and using said sinuosity s to determine the distances d.

18. The computer readable program product according to claim 17, wherein the using the timer counts T and the time delay Δt to determine the distances d further includes determining the distances d using the equation: $T=\Delta t+d/s$.

19. The computer readable program product according to claim 16, wherein the time delay Δt is 0.1 μs.

20. The computer readable program product according to claim 16, wherein the using said determined distances d to determine an increase in a distance the pedestrian walks on the path to avoid the obstacles includes using the determined distances d to compute an average length L for a stride of the pedestrian.

* * * * *

UNITED STATES PATENT AND TRADEMARK OFFICE
CERTIFICATE OF CORRECTION

| | | |
|---|---|---|
| PATENT NO. | : 10,852,144 B2 | Page 1 of 1 |
| APPLICATION NO. | : 16/531999 | |
| DATED | : December 1, 2020 | |
| INVENTOR(S) | : Frederic Bauchot and Jean-Yves Clement | |

It is certified that error appears in the above-identified patent and that said Letters Patent is hereby corrected as shown below:

In the Claims

Column 10, Line 27; In Claim 1, delete "Tat" and insert --T at-- therefor

Column 12, Line 28; In Claim 16, delete "Tat" and insert --T at-- therefor

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*